United States Patent [19]
Scheier et al.

[11] Patent Number: 4,852,143
[45] Date of Patent: Jul. 25, 1989

[54] ORAL X-RAY PACKET CUSHION AND PACKET EMBODYING THE SAME

[76] Inventors: Paul A. Scheier; Louise E. Scheier, both of 220 Central Park South, New York, N.Y. 10019

[21] Appl. No.: 114,446

[22] Filed: Oct. 28, 1987

[51] Int. Cl.4 ........................ A61B 19/04; G03B 42/02
[52] U.S. Cl. .................................... 378/168; 378/184; 433/136
[58] Field of Search ................................ 378/168–170, 378/184; 433/136, 140

[56] References Cited

U.S. PATENT DOCUMENTS

| | | | |
|---|---|---|---|
| 1,994,579 | 3/1935 | Hogdson | 378/169 |
| 4,071,955 | 2/1978 | Julius | 433/136 |
| 4,626,216 | 12/1986 | Strong-Grainger | 433/229 |

*Primary Examiner*—Carolyn E. Fields
*Assistant Examiner*—Joseph A. Hynds
*Attorney, Agent, or Firm*—Edgar N. Jay; Vincent T. Pace

[57] ABSTRACT

A cushioned oral X-ray plate packet as well as a cushion for use with an X-ray plate packet are provided. The cushion is made of compressed cellulose sponge material which expands in thickness when moistened. A cushion wrap is also disclosed for controlling the wetting and/or expansion of the cushion.

7 Claims, 1 Drawing Sheet

ORAL X-RAY PACKET CUSHION AND PACKET EMBODYING THE SAME

BACKGROUND OF THE INVENTION

This invention relates to X-ray film or plate packets for use in taking dental X rays and more particularly, to an improved cushion for such packets and an oral X-ray packet embodying such a cushion.

Dental X-ray film plates are formed of relatively rigid material which must be carefully positioned in the mouth of the patient if the resulting X-ray photograph is to have the required resolution of the desired area. It has long been recognized that such plates when placed in the sensitive areas of a patient's mouth can and often do cause considerable discomfort. There have been many attempts to deal with the problem. For example, Bolin U.S. Pat. No. 1,631,497 granted on May 12, 1925, relates to an X-ray film package having a container for holding the film and which consists of a frame having a back and marginal portions forming enlarged beading, the container being formed entirely of resilient material such as elastic rubber so that the marginal beading exerts pressure to retain the film between itself and the back of the container. Marler U.S. Pat. No. 1,631,497, granted June 7, 1927, like Bolin, relates to the use of rubber beading but in the form of a rubber band which is to be stretched and snapped around the edges of the sheets to form the desired X-ray packet with the tension at the edges of the band serving to draw it down over the margins of the sheets. Hillman U.S. Pat. No. 1,698,795, granted Jan. 15, 1929, relates to a dental X-ray film holder which consists of a single piece of any suitable soft, flexible material, preferably rubber. Hodgson U.S. Pat. No. 1,994,579 granted Mar. 19, 1935 relates to an X-ray dental package to one face of which is secured a pad of an absorbent material which may be formed of one or more layers of absorbent cotton, the pad extending a short distance beyond the edge of the film package. Van Valkenburg U.S. Pat. No. 2,020,281, granted Aug. 6, 1935, relates to a reusable bite wing support or holder for X-ray film packages in which the reusable support is made of any suitable material such as rubber or other slightly flexible material such as Bakelite (or other phenolic condensation product). Kenney U.S. Pat. No. 2,084,092, granted June 15, 1937, relates to a dental film packet holder made of stretchable rubber and having an integral bite wing.

All such devices have left much to be desired. Such devices as hitherto constructed have not been as effective as desired in minimizing the discomfort associated with the positioning of an X-ray film package in the sensitive areas of the mouth of a patient. That has been largely the result of the difficulty encountered when attempting to position the film package in the optimum position for a given X ray. Not only is the patient's discomfort a serious factor but also in some instances the discomfort may be so great as to prevent proper positioning.

SUMMARY OF THE INVENTION & DRAWINGS

It is therefore, a principal object of this invention to provide an oral X-ray packet which more readily lends itself to be positioned precisely where required in the mouth of a patient with substantially reduced discomfort for the patient than hitherto attainable.

A more specific object of this invention is to provide such an X-ray film packet which at the time of insertion into the mouth of the patient is readily deformable so as to be readily and accurately positioned in the mouth of a patient.

Another object is to provide a uniquely improved cushion for use with dental X-ray packets which facilitate insertion of the packet into the mouth of a patient with greatly enhanced freedom from discomfort.

The present invention stems from the discovery that the use of a material that expands substantially only unidirectionally provides an X-ray packet and cushion therefore having unique properties suitable for ready insertion into a patient's mouth with greatly reduced pain or discomfort than heretofore.

Further objects as well as features of the present invention will be apparent from the following detailed description of preferred embodiments thereof and the accompanying drawings in which.

DESCRIPTION OF THE INVENTION

Referring now to FIGS. 1–3A of the drawings, dental X-ray film packet 10 includes an X-ray film or sensitized plate enclosed in a thin plastic envelope 12 and a perimeter cushion 14 formed to fit around the edges of the envelope 12 as shown. Preferably, cushion 14 is affixed to the envelope 12, as by a suitable adhesive. The width of the perimeter cushion 14 is preferably narrow so that only the peripheral portion of the envelope 12 is covered, thereby limiting the volume of the X-ray film package 10 when the cushion is moistened. It is an important feature of this invention that the material of which the cushion 14 is formed expands substantially unidirectionally as it is wet by a suitable liquid such as water. This property is used advantageously in accordance with the present invention by arranging the material of which the cushion 14 is formed so that when wet the cushion expands its thickness in a direction that is generally perpendicular to the surface of the envelope 12 to which it is attached. The preferred material used is commercially available as hydraulically compressed cellulose sponge No. 65025 from Spontex, located in Columbia, Tenn., in sheet form about 0.125 inch thick and, if unrestricted, expands when moistened to about 5 times its dry thickness. It is also contemplated that material with less expandability, about three times its dry thickness or greater expandability, up to about 1.25 inch in thickness can be used. Thus, it is practical to store the film packet 10 as a unit with the cushion 14 dry.

In use, the cushion 14 of the X-ray packet 10 is wet with any suitable liquid and is then readily placed in the desired position in the mouth of the patient. For example, in one embodiment, the perimeter cushion 14 while unmoistened added no more than about 0.25 inch to the thickness of the peripheral area of the X-ray packet 10 but when fully wet expanded to about five times that thickness.

Instead of providing the cushion 14 affixed to the X-ray envelope 12 as an integral part of the X-ray packet 10, the cushion 14 may be stored separately for use when required. In that event, cushion 14 may be used with or without an adhesive to bond it to the envelope 12. It is also contemplated that a suitable bonding agent may be applied to cushion 14 so that it is fixed to the envelope 12, more or less permanently, as desired.

Figure 1:
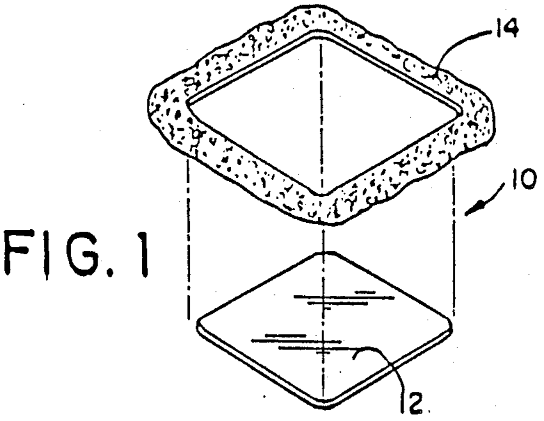
FIG. 1 is an exploded view of a cushioned oral X-ray plate according to the invention.
Figure 3A:
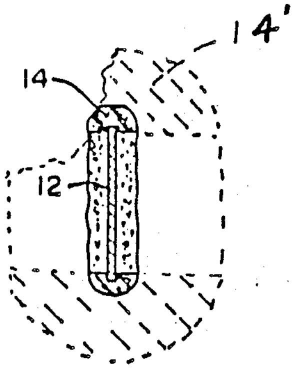
FIG. 3A is a cross sectional view of the cushioned oral X-ray plate of FIG. 2 as viewed through the line 3-3 and with the expanded cushion shown in dashed lines.
Figure 2:
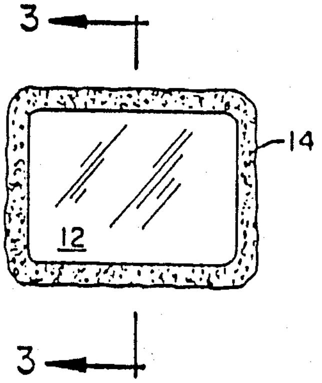
FIG. 2 is a plan view of the dental X-ray plate of FIG. 1 when assembled.
Figure 3B:
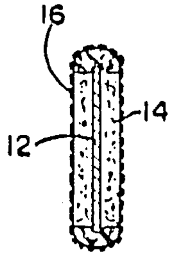
FIG. 3B is a view similar to FIG. 3A showing an embodiment having a perforated enclosure.

In accordance with a further embodiment of this invention, the X-ray package 10 with the cushion 14 thereon, is enclosed in a perforated outer wrap 16, as shown in FIG. 3B, made of a water-impervious, readily stretchable elastic material perforated so as to control wetting of the cushion 14 and thereby the expansion of the cushion. By applying a small controlled amount of liquid to one or more of the holes in the wrap 16, swelling or expansion of a small part of the cushion can be induced. Swelling can thus be limited to as small an area of the surface of the cushion 14 as may be desired. The volume enclosed by the wrap 16 is restricted to less than that to which the fully wet cushion can expand when it is desired to restrict the expansion of the cushion 14. When a relatively inelastic material such as cellophane or the like is used to form the wrap 16, then gussets are provided therein as required.

Figure 4:
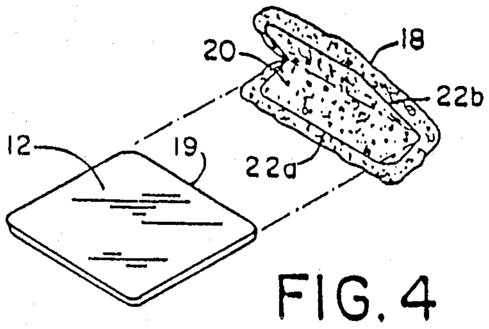
FIG. 4 is an exploded view of another embodiment of the subject invention showing a single edge cushion.

Because the wet and expanded material of which cushion 14 is fabricated is soft and readily deformable under extremely light forces, it lends itself to use when it is necessary to place an X-ray package 10 in an area where the dental patient is extremely sensitive. It may also be desirable to restrict the surface of the package 10 to which a cushion is applied. To that end another embodiment, shown in FIG. 4, is contemplated in which an edge cushion 18 is formed to be folded over a single edge 19 of the film plate 12. Cushion 18 has an adhesive 20 on its contact surfaces **22*a*, 22*b* by which the cushion 18 is affixed to the edge 19 of the film envelope 12. In this manner, one or more edge cushions 18 may be applied to an X-ray film envelope 12** to alleviate patient discomfort.

Cushioned oral X-ray packets as well as cushions adapted to be affixed to X-ray packets made in accordance with this invention are advantageously used to provide increased comfort for dental patients. The cushioned material in its dry state occupies a very small volume and when wet softens and expands to alleviate discomfort from the relatively hard or sharp edges of the film envelope. The cushion is easily affixed to the edges of the film plate envelope 12 and when desired can be readily removed from the X-ray envelope.

The terms and expressions which have been employed are used as terms of description and not of limitation. There is no intention in the use of such terms and expressions of excluding any equivalents of the features shown and described, or portions thereof. It is to be recognized, however, that various modifications are possible within the scope of the invention claimed.

What is claimed is:

1. An oral X-ray film packet, comprising an oral X-ray film plate and enclosure, and a soft expandable elongated cushion disposed around an edge of an outer surface of said enclosure, said cushion being formed of compressed cellulose which when wet expands substantially unidirectionally perpendicular to the surface of said enclosure.

2. An oral X-ray film packet as set forth in claim 1 wherein said cushion extends about the entire perimeter of said enclosure.

3. An oral X-ray film packet as recited in claim 1 wherein said cushion is enclosed in a perforated wrapping for controlling the absorption of moisture by said cushion, wherein the expansion of said cushion is controlled.

4. An oral X-ray film packet as recited in claim 1 wherein said cushion had a width which is small relative to that of said X-ray film plate.

5. An oral X-ray packet cushion comprising an elongated member formed to engage at least a peripheral portion of an oral X-ray packet in predetermined relation, said member being formed of a dry compressed cellulose sponge material which when wet while in said predetermined relation expands unidirectionally in a direction normal to an enclosed portion of said packet.

6. An oral X-ray packet cushion as set forth in claim 5 in which said member forms an opening for receiving the entire perimeter of said packet.

7. An oral X-ray packet cushion as set forth in claim 5 in which said member is enclosed in a perforated wrapping for controlling the absorption of moisture by said member, wherein the expansion of said member is controlled.

* * * * *